(12) United States Patent
Rodefeld et al.

(10) Patent No.: US 6,204,413 B1
(45) Date of Patent: Mar. 20, 2001

(54) PROCESS FOR THE PREPARATION OF SALTS OF 1-SUBSTITUTED 2,4-DIAMINOBENZENES

(75) Inventors: Lars Rodefeld, Leverkusen; Alexander Klausener, Pulheim; Horst Behre, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/547,310

(22) Filed: Apr. 11, 2000

(30) Foreign Application Priority Data

Apr. 22, 1999 (DE) ................................ 199 18 293

(51) Int. Cl.$^7$ .................................. C07C 209/00
(52) U.S. Cl. ..................... 564/418; 564/420; 564/421; 564/422; 564/423
(58) Field of Search ............................ 564/418, 420–423

(56) References Cited

U.S. PATENT DOCUMENTS

| | | | |
|---|---|---|---|
| 2,988,571 | 6/1961 | MacFie et al. | 260/613 |
| 4,125,367 | 11/1978 | Bugaut et al. | 8/11 |
| 4,259,261 | 3/1981 | Bugaut et al. | 564/99 |
| 4,329,504 | 5/1982 | Bugaut et al. | 564/443 |
| 4,854,935 | 8/1989 | Clausen et al. | 8/408 |
| 5,002,585 | 3/1991 | Junino et al. | 8/411 |
| 5,078,748 | 1/1992 | Akram | 8/405 |
| 5,084,067 | 1/1992 | Junino et al. | 8/421 |

FOREIGN PATENT DOCUMENTS

| | | |
|---|---|---|
| 2291184 | 11/1974 | (FR) . |
| 1591663 | 6/1981 | (GB) . |
| 1597034 | 9/1981 | (GB) . |

OTHER PUBLICATIONS

J. Chem. Soc., 1921, (119) pp. 2076–2078, A New Synthesis of Oxazines, Fairbourne et al.

*Primary Examiner*—Samuel Barts
(74) *Attorney, Agent, or Firm*—Joseph C. Gil; Diderico van Eyl

(57) ABSTRACT

The invention relates to a process for the preparation of specific salts of 1-substituted 2,4-diaminobenzenes by catalytic hydrogenation of 1-substituted 2,4-dinitrobenzenes and addition of the reaction product obtained after the hydrogenation and separated from the catalyst to an aqueous solution of an acid.

12 Claims, No Drawings

PROCESS FOR THE PREPARATION OF SALTS OF 1-SUBSTITUTED 2,4-DIAMINOBENZENES

BACKGROUND OF THE INVENTION

The present invention relates to a process for the preparation of salts of 1-substituted 2,4-diaminobenzenes by catalytic hydrogenation of the corresponding 1-substituted 2,4-dinitrobenzenes and conversion of the resulting reaction product, following removal of the catalyst, into the salt form.

Salts of 1-substituted 2,4-diaminobenzenes are used in many different areas. Their synthesis is therefore of particular importance. 2-(2',4'-diamino-diaminophenoxy)-ethanol and its salts are used, for example, according to DE-A-27 58 735 and DE-A-27 37 138, in oxidation dye compositions as the meta-component.

DE-A-27 58 735 describes the preparation of 2-(2',4'-diaminophenoxy)-ethanol by catalytic hydrogenation of 2-(2',4'-dinitrophenoxy)-ethanol. To remove the catalyst, the reaction mixture after the hydrogenation is filtered in the warmed state, and the filtrate is recovered. To prepare the dihydrochloride salt of 2-(2',4'-diaminophenoxy)-ethanol, an excess of hydrogen chloride gas is then introduced into the filtrate. However, this method produces a yield of only 78%. Reworking this process also shows that the product is produced in a deep violet color and contains considerable amounts of by-products and decomposition products, which is manifested in a purity of only 86%. Measurement of the degrees of transmission of a 0.1% strength solution of the product in water according to DIN 55945 gives the results $T_x=38.6$, $T_y=26.4$ and $T_z=30.9$.

Particularly when the salts of the 1-substituted 2,4-diaminobenzenes, such as 2-(2',4'-diaminophenoxy)-ethanol, are used in the cosmetics sector, e.g., as precursor compounds in the field of hair cosmetics, the purity of the 1-substituted 2,4-diaminobenzenes is a decisive factor: even slight contamination by foreign substances is problematical for medicinal reasons (e.g., danger of triggering allergies).

The object of the present invention was therefore to provide a process with which salts of 1-substituted 2,4-diaminobenzenes and in particular of 2-(2',4'-diaminophenoxy)-ethanol can be obtained with low impurities and low undesired discoloration.

DESCRIPTION OF THE INVENTION

The above-mentioned object is achieved by a process for the preparation of salts of 1-substituted 2,4-diaminobenzenes of the formula (I)

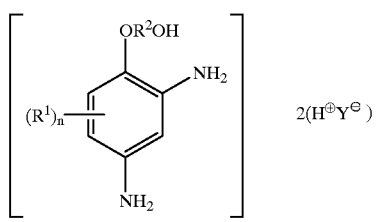

(I)

wherein each $R^1$ is a linear or a branched $C_1$–$C_{20}$-alkyl group, a $C_6$–$C_{18}$-aryl group, a $C_2$–$C_{20}$-acyl group, a COOH group, a COOR$^3$ group in which $R^3$ is a linear or a branched $C_1$–$C_{20}$-alkyl radical, or $N(R^4)_2$, in which each $R^4$ is hydrogen, a linear or a branched $C_1$–$C_{20}$-alkyl radical or a $C_2$–$C_{20}$-acyl radical, and n is an integer from 0 to 3, $R^2$ is a radical of the formula (II)

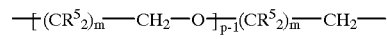

(II)

in which each $R^5$ is hydrogen or a $C_1$–$C_5$-alkyl radical, m is an integer from 1 to 12 and p is an integer from 1 to 4, or a radical of the formula (III),

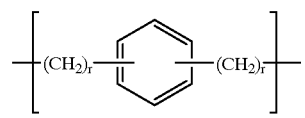

(III)

in which r is an integer from 0 to 2 and optionally one or more carbon atoms of the phenyl ring are replaced by N, O or S, and $Y^\ominus$ is the equivalent amount of a monovalent, divalent, or a trivalent anion.

Generally, the process involves the step of catalytically hydrogenating 1-substituted 2,4-dinitrobenzenes of the formula (IV),

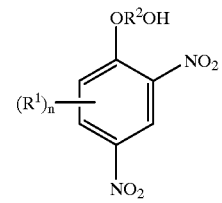

(IV)

in which $R^1$, n and $R^2$ have the meanings given for formula (I), and separating the reaction product obtained, after the hydrogenation, from the catalyst and adding the reaction product to an aqueous solution of an acid $H^\oplus Y^\ominus$, in which $Y^\ominus$ has the meaning given above. The process according to the invention is characterized in that the product of the formula (I) can be obtained in an excellent yield of at least 80%, preferably at least 85%, particularly preferably at least 89%, and also with a very high purity of up to 98% and an improved color.

In the 1-substituted 2,4-dinitrobenzenes of the formula (IV), each $R^1$ is preferably a linear or a branched $C_1$–$C_{10}$-alkyl group, a $C_6$–$C_{12}$-aryl group, a $C_2$–$C_6$-acyl group or a $N(R^4)_2$ group in which each $R^4$ is hydrogen, a linear or a branched $C_1$–$C_6$-alkyl radical or a $C_2$–$C_6$-acyl radical. In addition, n is preferably an integer from 0 to 2.

$R^2$ is preferably a radical of the formula (II) in which m is an integer from 1 to 9, in particular 1, 2 or 3, $R^5$ is hydrogen or methyl, and p is 1 or 2. Particularly preferably, the radical $R^2$ is —[CH$_2$—CH$_2$]—, —[CH(CH$_3$)—CH$_2$]— or —[CH$_2$—C(CH$_3$)$_2$—CH$_2$]—, where p is 1.

In addition, $R^2$ is preferably a radical of the formula (III), where r is 0 or 1. Particularly preferably, the radical $R^2$ is,

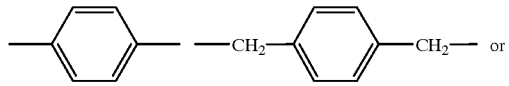

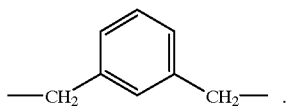

In particular, the process according to the invention has proven successful for preparing the salts of 2-(2',4'-diaminophenoxy)-ethanol from 2-(2',4'-dinitrophenoxy)-ethanol, where $Y^\ominus$ is preferably $Cl^\ominus$, $\frac{1}{2}(SO_4)^{2\ominus}$ or $\frac{1}{3}(PO_4)^{3\ominus}$.

A process for the preparation of 1-substituted 2,4-dinitrobenzenes of the formula (IV) is described in a German Patent Application filed on the same date. Other processes are known from DE-A-27 58 735, J. Chem. Soc. 1921 (119), 2076-8 and U.S. Pat. No. 2,988,571.

The hydrogenation of the 1-substituted 2,4-dinitrobenzenes according to formula (IV) is carried out in the presence of hydrogenation catalysts, which are sufficiently known to the person skilled in the art. Examples of such catalysts include noble metal catalysts based on platinum or palladium. It is also possible to use Raney nickel or Raney cobalt catalysts, which can, if appropriate, be alloyed with other metals such as molybdenum, titanium, vanadium, magnesium, iron or chromium. The hydrogenation catalysts can be supported or unsupported.

The hydrogenation is generally carried out in the presence of a solvent. Examples of suitable solvents are branched or unbranched aliphatic alcohols, preferably isopropanol, and optionally substituted aromatic hydrocarbons such as toluene or chloroaromatics. The hydrogenation is generally carried out at a hydrogen pressure of 0.1 to 10 MPa, preferably 0.5 to 5 MPa and at a temperature of 20 to 150° C., preferably 40 to 120° C.

The reaction product obtained after the hydrogenation of the 1-substituted 2,4-dinitrobenzenes of the formula (IV) is separated from the catalyst and is introduced into an aqueous solution of an acid $H^\oplus Y^\ominus$, in which $Y^\ominus$ is the equivalent amount of a monovalent, divalent or trivalent basic acid anion.

The acid $H^\oplus Y^\ominus$ is preferably hydrochloric acid, sulphuric acid or phosphoric acid, e.g, $Y^\ominus$ is $Cl^\ominus$, $\frac{1}{2}(SO_4)^{2\ominus}$ or $\frac{1}{3}(PO_4)^{3\ominus}$. The acid $H^\oplus Y^\ominus$ is introduced in an amount such that the molar ratio of the acid $H^\oplus Y^\ominus$, to the reaction product of the hydrogenation, i.e., the 1-substituted 2,4-diamino-benzene, is at least 2:1.

It has also proven successful to add the reaction product obtained after the hydrogenation and separated from the catalyst to an initial charge which includes not only the aqueous solution of the acid $H^\oplus Y^\ominus$, but also a solvent which is miscible with the acid $H^\oplus Y^\ominus$ water. Preference is given to using isopropanol as such a solvent. As a result, a further increase in the yield can be achieved. It has proven successful to carry out the reaction using an inert gas.

The invention provides numerous advantages. For instance, unlike the process in DE-A-27 58 735 discussed in the Background of the Invention) the present invention avoids the low yields obtained by this process as well as avoids the deep violet color containing considerable amounts of by-products and decomposition products. As such, the invention provides a valuable process for preparing an important class of compounds.

The invention is further illustrated but is not intended to be limited by the following examples in which all parts and percentages are by weight unless otherwise specified.

EXAMPLES

Example 1

A 1 l autoclave reactor was filled with 120 g of 2-(2',4'-dinitrophenoxy)ethanol, 3 g of a 1% platinum/carbon catalyst which included 50% water, and 400 ml of isopropanol. At a hydrogen pressure of 1 MPa and a temperature of 100° C., hydrogenation was carried out for 10 h. The system was then cooled to 20° C., and the reaction mixture was added dropwise under a nitrogen atmosphere through a filter into an initial charge of 240 g of 37% strength hydrochloric acid which had been previously flushed repeatedly with nitrogen. The resulting suspension was heated at reflux temperature for about 30 min and then cooled to 10° C. The product obtained after filtration was washed once with isopropanol to give 113.1 g of 2-(2',4'-diamino-phenoxy)ethanol (89.1% yield) in 98% purity. Measuring the degrees of transmission of a 0.1% strength solution of the product in water in accordance with DIN 55945 gave, as results, $T_x$=99.4, $T_y$=98.9 and $T_z$=98.2.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a salt of 1-substituted 2,4-diaminobenzenes of the formula (I)

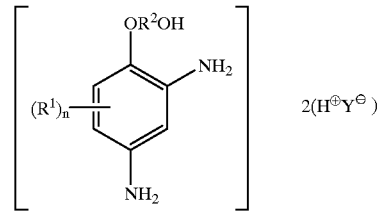

wherein each $R^1$ is a component comprising a member selected from the group consisting of linear $C_1$–$C_{20}$-alkyl groups, branched $C_1$–$C_{20}$-alkyl groups, $C_6$–$C_{18}$-aryl groups, $C_2$–$C_{20}$-acyl groups, COOH groups, $COOR^3$ groups; wherein $R^3$ is a linear or a branched $C_1$–$C_{20}$-alkyl radical, or a $N(R^4)_2$ group, in which each $R^4$ is hydrogen, a linear or a branched $C_1$–$C_{20}$-alkyl radical or a $C_2$–$C_{20}$-acyl radical, and n is an integer from 0 to 3;

$R^2$ is a radical of the formula (II)

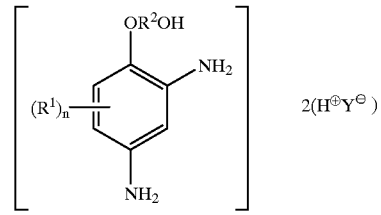

wherein each $R^5$ is hydrogen or a $C_1$–$C_5$-alkyl radical, m is an integer from 1 to 12 and p is an integer from 1 to 4, or a radical of the formula (III),

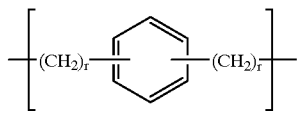

(III)

wherein each r is an integer from 0 to 2 and optionally one or more carbon atoms of the phenyl ring are replaced by N, O or S, and $Y^\ominus$ is an equivalent amount of a monovalent, divalent or a trivalent basic acid anion;

the process comprising the steps of
A) catalytically hydrogenating a 1-substituted 2,4-dinitrobenzenes of the formula (IV) in the presence of a catalyst,

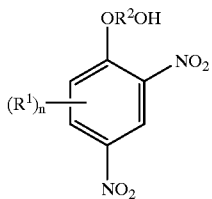

(IV)

wherein $R^1$, n and $R^2$ have the meanings given for formula (I) to form a reaction product; and
B) separating the reaction product obtained after hydrogenation of 1-substituted 2,4-dinitrobenzenes of the formula (IV) from the catalyst and adding the reaction product to an aqueous solution of an acid $H^\oplus Y^\ominus$, wherein $Y^\ominus$ has the meaning given above.

2. The process of claim 1, wherein in the formula (I), each $R^1$ is a component comprising a member selected from the group consisting of linear $C_1$–$C_{10}$-alkyl groups, branched $C_1$–$C_{10}$-alkyl groups, $C_6$–$C_{12}$-aryl groups, $C_2$–$C_6$-acyl groups and $N(R^4)_2$ groups, in which each $R^4$ is hydrogen, a linear or a branched $C_1$–$C_6$-alkyl radical or a $C_2$–$C_6$-acyl radical, and independently thereof n is an integer from 0 to 2.

3. The process of claim 1, wherein in formula (I), $R^2$ is a radical of the formula (II), in which m is an integer from 1 to 9, $R^5$ is hydrogen or methyl, and p is 1 or 2.

4. The process of claim 3, wherein m is 1, 2 or 3.

5. The process of claim 1, wherein the radical $R^2$ in the formula (II) is —[$CH_2$—$CH_2$]—, —[$CH(CH_3)$—$CH_2$]— or —[$CH_2$—$C(CH_3)_2$—$CH_2$]—, in which p is 1.

6. The process of claim 1, wherein $R^2$ is a radical of the formula (III), in which r is 0 or 1.

7. The process of claim 6, wherein the radical $R^2$ is

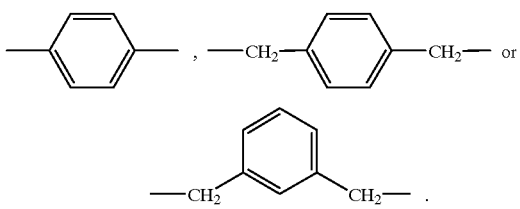

8. The process of claim 1, wherein the hydrogenation of the 1-substituted 2,4-dinitrobenzenes of the formula (IV) is carried out in the presence of a catalyst component comprising a member selected from the group consisting of noble metal catalysts based on platinum, noble metal catalysts based on palladium, Raney nickel catalysts, and Raney cobalt catalysts.

9. The process of claim 1, wherein the hydrogenation is carried out at a hydrogen pressure ranging from about 0.1 to about 10 MPa at a temperature ranging from about 20 to about 150° C.

10. The process of claim 9, wherein the process is carried out at a hydrogen pressure ranging from about 0.5 to about 5 MPa at a temperature ranging from about 40 to about 120° C.

11. The process of claim 1, wherein the acid $H^\oplus Y^\ominus$ is an acid comprising a member selected from the group consisting of hydrochloric acid, sulphuric acid and phosphoric acid.

12. The process of claim 1, wherein the salt of 1-substituted 2,4-diamino-benzenes of the formula (I) produced is the salt of 2-(2',4'-diaminophenoxy)-ethanol.

* * * * *